United States Patent [19]

Iinuma et al.

[11] Patent Number: 5,112,327
[45] Date of Patent: May 12, 1992

[54] DOUBLE-SIDED NEEDLE ASSEMBLY

[75] Inventors: Mitsuhisa Iinuma, Nagoya; Hideo Yamada; Hiroaki Matsushima, both of Nishinomiya; Hisao Tobiki, Kobe, all of Japan

[73] Assignee: Nihon Medi-Physics Co., Ltd., Takarazuka, Japan

[21] Appl. No.: 456,956

[22] Filed: Dec. 26, 1989

[30] Foreign Application Priority Data

Jan. 18, 1989 [JP] Japan ................... 1-4047[U]
Sep. 29, 1989 [JP] Japan ................. 1-114829[U]

[51] Int. Cl.$^5$ .................................. A61B 19/00
[52] U.S. Cl. ............................. 604/413; 604/240; 604/264; 128/763
[58] Field of Search ............... 128/763-767; 604/237, 413, 240, 263, 264

[56] References Cited

U.S. PATENT DOCUMENTS

| | | | |
|---|---|---|---|
| 3,063,450 | 11/1962 | Myerson et al. | 128/218 |
| 3,096,763 | 7/1963 | McConnaughey | 128/221 |
| 3,494,352 | 2/1970 | Russo et al. | 128/2 |
| 3,585,984 | 6/1971 | Buchanan | 128/2 |
| 3,848,579 | 11/1974 | Villa-Real | 128/2 F |
| 3,974,832 | 8/1976 | Kruck | 128/221 |
| 4,170,994 | 10/1979 | Komatsu | 604/251 |
| 4,755,173 | 7/1988 | Konopka | 604/180 |
| 4,772,265 | 9/1988 | Walter | 604/164 |
| 4,964,855 | 10/1990 | Todd et al. | 604/192 X |

FOREIGN PATENT DOCUMENTS

| | | |
|---|---|---|
| 0042088 | 12/1981 | European Pat. Off. . |
| 918060 | 2/1963 | United Kingdom . |
| 1444119 | 7/1976 | United Kingdom . |

Primary Examiner—Robert A. Hafer
Assistant Examiner—Kerry Owens
Attorney, Agent, or Firm—Jones, Tullar & Cooper

[57] ABSTRACT

A double-sided needle assembly includes an insert needle for inserting into a vessel; an afflux needle for supplying pharmaceutical liquid in an injector to the insert needle; and a luer member. The member connects the insert needle with the afflux needle through a space defined between the ends of the needles in the member, and holds the insert and afflux needles to fit to the syringe of the injector under pressure. The confirmation of the insertion of the insert needle into the vessel is accomplished by observing the space of the luer member.

4 Claims, 5 Drawing Sheets

DOUBLE-SIDED NEEDLE ASSEMBLY

CROSS-REFERENCE TO RELATED APPLICATION

This application contains subject matter in common with copending application, Ser. No. 07/320,608, now U.S. Pat. No. 5,017,191.

BACKGROUND OF THE INVENTION

The present invention relates to a medical needle assembly, and more specifically, relates to a special double-sided needle assembly.

FIG. 1 shows a conventional injector used to administer a pharmaceutical liquid into a human body, i.e., in the case where an injector already filled with pharmaceutical liquid, a so-called "pre-filled syringe". The injector shown in FIG. 1 is constructed in such a way that a conventional type double-sided needle 1 is fitted to a syringe 4 with a stopper 3. In this type of needle 1, a plunger (not shown) of the injector is drawn to observe back-flow of the blood, and based on the observation, an operator makes a decision whether or not the needle 1 has been inserted in the vessel of the body. However, the operator can not confirm this fact until the blood comes into the syringe 4 of the injector through the needle 1.

FIG. 2 shows a normal needle 5 which is also used for a syringe 7 wherein blood can be observed at a space 6 to thereby confirm the insertion of the needle 5.

On the other hand, in a case where a radiopharmaceutical including radioisotope is administered into a patient, in order to protect administering operators such as physicians and nurses from the radiation exposure thereof on administration, a lead shield member 8 partially provided with a lead glass window 9 (referred to hereinafter as a "syringe shield") as shown in FIG. 3 is normally used. When the radiopharmaceutical in the pre-filled syringe is administered through the use of the syringe shield 8, the operators confirm entry of blood through the glass window 9 thereof. However, it is very difficult to observe the inside of the syringe because of the yellowish color of the glass window 9, which is not a colorless transparent color, and the darkness inside of the syringe. Therefore, it takes a long time to confirm insertion of the needle, resulting in an increment of exposure to the operators. If in order to protect the operators from exposure, insertion is confirmed based on the feelings of the operators, the patients are unnecessarily subjected to a possible in failure of insertion.

In order to resolve such disadvantages, firstly, a procedure is devised in which the confirmation can be accomplished at the same portion as the space 6, as shown in FIG. 2, of a normal luer needle and outside the syringe. The idea is described hereinbelow. Two kinds of special needles shown in FIGS. 4 and 5 (referred to hereinafter as a "double luer needle" are proposed and then a manner for accomplishing the confirmation of the insertion of the needles into the vessel is proposed in which widely used disposable needles can be used confirmation of blood can be accomplished at the luer member of each needle. However, since the needle shown in FIG. 4, has three parts in assembly, a luer cap 2, namely a double luer needle 10, and a disposable needle (not shown), to form the luer member, the length of the needle portion thereof composed by the double luer needle 10 and the disposable needle is increased, resulting in difficulty in administering a pharmaceutical liquid. On the other hand, with the needle shown in FIG. 5, the technique for performing a firm engagement between a double luer needle 11 and a luer cap 2 is difficult, and even though the engagement is performed, it results in a very high cost lacking practical use.

SUMMARY OF THE INVENTION

Accordingly, an essential object of the present invention is to resolve these disadvantages and to provide a double-sided needle assembly which reduces the length of the needle portion thereof, and is capable of easily being fitted to a syringe of an injector, resulting in a compact construction, and accomplishing confirmation.

In accomplishing this and other objects, according to one preferred embodiment of the present invention, there is provided a double-sided needle assembly comprising: an insert needle for inserting into a vessel; an afflux needle for supplying pharmaceutical liquid in a syringe of an injector to the insert needle; and a transparent luer member connecting the insert needle with the afflux needle through a space defined between an end of the insert needle and an end of the afflux needle in the luer member, and holding the insert and afflux needles to fit to the syringe.

By the above construction of the present invention, since the space for observing the back-flow of blood is arranged between the end of the insert needle and the end of the afflux needle in the luer member, confirmation of insertion of the insert needle into a vessel can be conveniently accomplished through the space in the luer member. Then, in the case of administration of pharmaceutical liquid, the radiation exposure of the operators can be certainly reduced by the use of the needle assembly. Furthermore, the length of the needle portion composed by the insert needle and the afflux needle is as small as that of a conventional normal disposable needle. The needle assembly can be very compact in construction, and can be fitted to a syringe of an injector by pressing at one time for completion for preparation of the use.

BRIEF DESCRIPTION OF THE DRAWINGS

These and other objects and features of the present invention will become clear from the following description taken in conjunction with the preferred embodiments thereof with reference to the accompanying drawings, in which.

DETAILED DESCRIPTION OF THE ILLUSTRATED EMBODIMENTS

Figure 1:
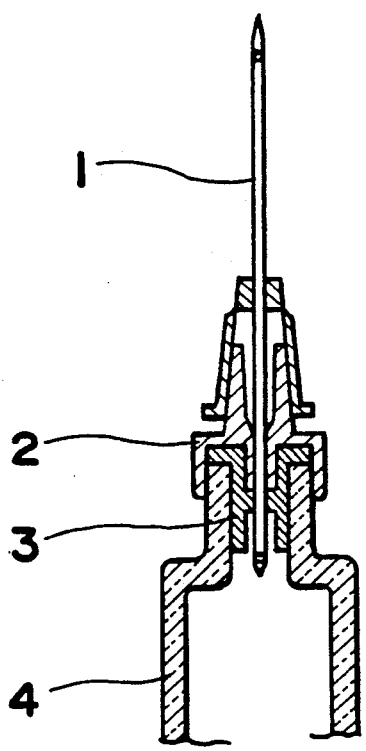
FIG. 1 is a partial sectional view of an injector fitting a double-sided conventional needle to a pre-filled syringe.
Figure 2:
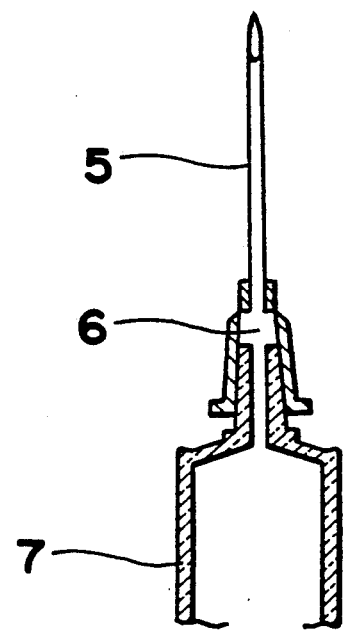
FIG. 2 is a partial sectional view of an injector fitting a normal needle to a normal syringe.
Figure 3:
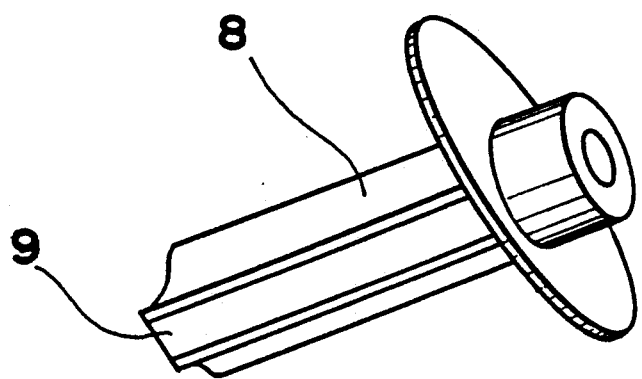
FIG. 3 is a perspective outside view of a syringe shield.
Figure 4:
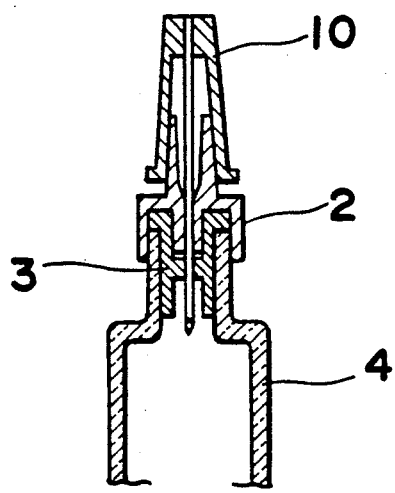
FIGS. 4 and 5 are partial sectional views of injectors fitting improved double luer needles to pre-filled syringes, respectively.
Figure 5:
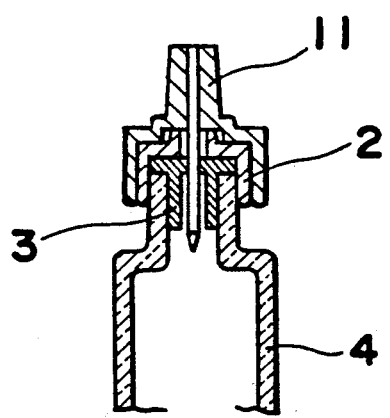

Before the description of the present invention proceeds, it is to be noted that like parts are designated by like reference numerals throughout the accompanying drawings.

Figure 6:
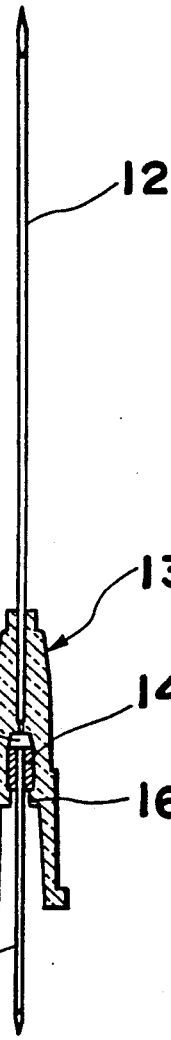
FIG. 6 is a sectional view of a double-sided needle assembly of a preferred embodiment according to the present invention.

As shown in FIG. 6, the kind of parts of a double-sided needle assembly of the preferred embodiment according to the present invention is generally the same as that of a commercial disposable needle, except for a cylinder 14 and an afflux needle 15. The assembly is manufactured in a similar manner.

The needle assembly includes an insert needle 12 for inserting into a vessel; an afflux needle 15 for supplying pharmaceutical liquid in an injector (not shown) to the insert needle 12; and a transparent luer member 13. The luer member 13 connects the insert needle 12 with the afflux needle 15 through a space 17 defined in the luer member 13, and holds both needles 12 and 15 to fit to the syringe of the injector. Therefore, the luer member 13 has a tapered hole for fitting to the syringe at the lower portion thereof in FIG. 6.

Figure 7:
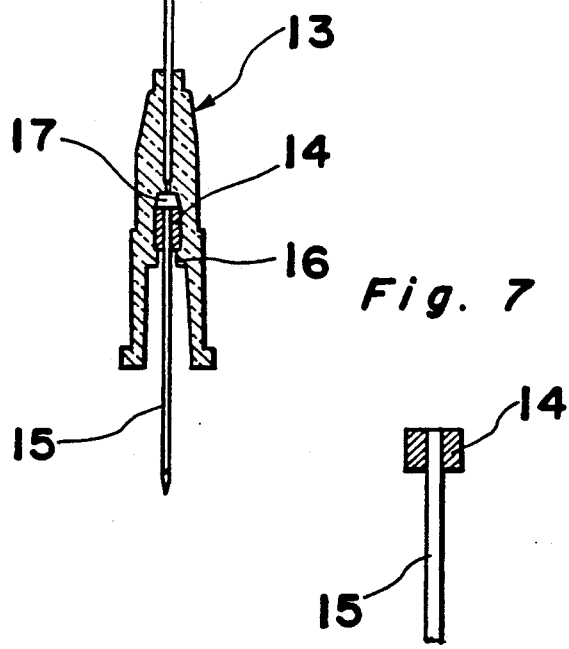
FIG. 7 is a sectional view of the upper end of an afflux needle of the needle assembly shown in FIG. 6.

The luer member 13 has a lower hole for inserting the afflux needle 15, and an upper hole for inserting the insert needle 12. The luer member 13 preferably has a rib 16 for preventing the afflux needle 15 from easily slipping off from the luer member 13 after the insertion of the afflux needle 15 into the luer member 13. The afflux needle 15 is shown in FIG. 7 and is manufactured separate from the other parts. A cylinder 14, serving as a connecting member, is fixed to the upper end of the afflux needle 15 in FIG. 6. The lower end of the insert needle 12 is fixedly inserted into the upper hole of the luer member 13 in FIG. 6. The cylinder 14 of the afflux needle 15 is fixedly inserted into the lower hole of the luer member 13. Then, the cylinder 14 adheres to the luer member 13 to define the space 17 between the lower end of the insert needle 12 and the upper end of the afflux needle 15 in the luer member 13. If the luer member 13 can be fixedly connected with the cylinder 14, the adhesive and/or the rib 16 is unnecessary. The luer member 13 is fitted to the syringe of the injector.

By the arrangement shown, the following advantages are obtained. Since the space 17 for observing the backflow of blood is arranged between insert needle end and the afflux needle end in the transparent luer member 13, the confirmation of the insertion of the insert needle 12 into a vessel can be conveniently performed through observation of the space 17 of the luer member 13. Then, in administering pharmaceutical liquid, the radiation exposure to the operators can be certainly reduced by the use of the double-sided needle assembly. Furthermore, the length of the needle portion composed by the insert needle 12 and the afflux needle 15 is as small as that of a conventional normal disposable needle and also the double-sided needle assembly can be very compact in construction. The double-sided needle assembly can be fitted to the syringe of the injector by pressing at one time for completion for preparation of the use.

Figure 8:
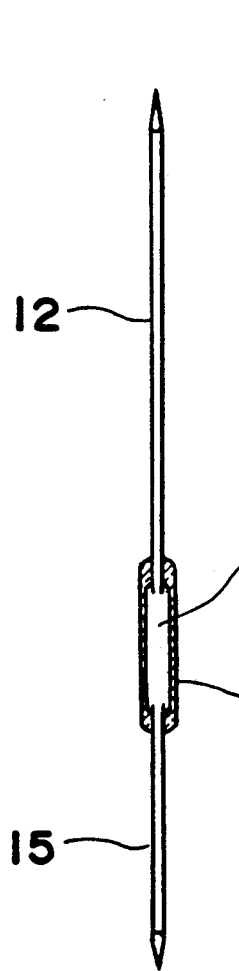
FIG. 8 is a sectional view of a double-sided needle assembly of another embodiment in which small needles are fitted to both ends of a transparent cylinder.
Figure 9:
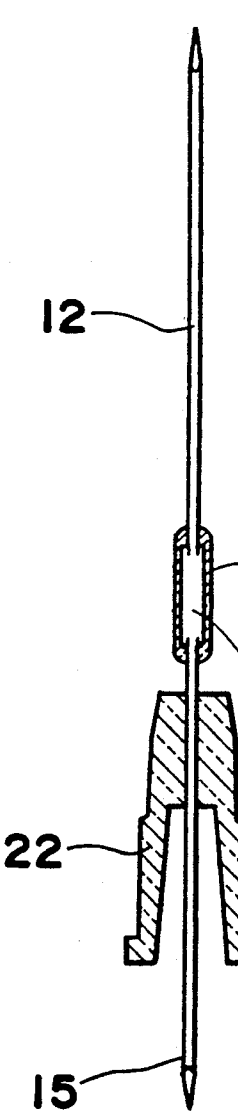
FIGS. 9 and 10 are sectional views in the conditions where the needle assembly with the small needles is being inserted into and is fitted to a transparent luer.
Figure 10:
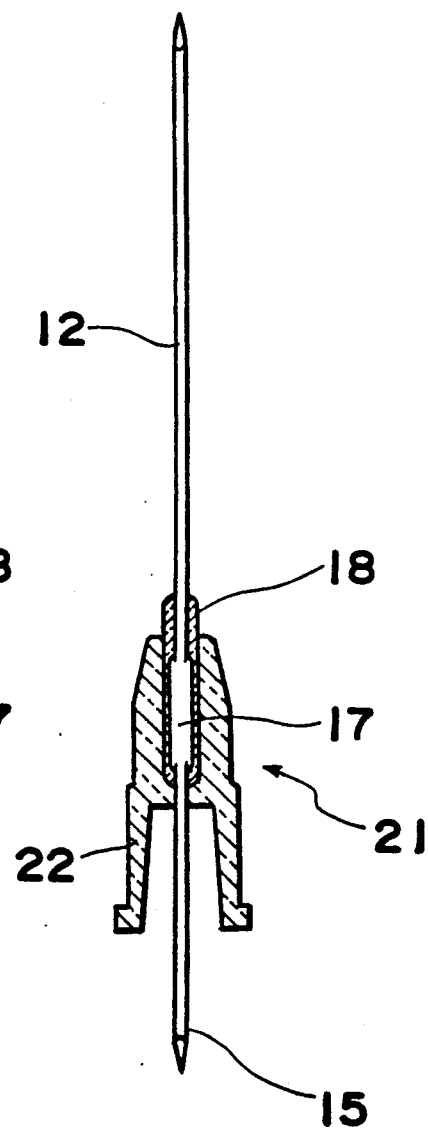

In another embodiment according to the present invention, as shown in FIG. 8, an insert needle 12 is previously connected with an afflux needle 15 through a transparent cylinder 18 to be integral with each other so that the space 17 can be defined between the needles 12 and in the cylinder 18. Then, as shown in FIGS. 9 and 10, these small double-sided needle parts are inserted into and adhered to a transparent luer 22, with the result that a similar needle assembly can be manufactured as the needle assembly of the first embodiment. In this embodiment, the luer member 21 is composed of the cylinder 18 and the luer 22. It is possible that the small double-sided needle parts shown in FIG. 8 can be inserted into the pre-filled syringe type luer cap 2 shown in FIG. 1 to obtain the same advantage as the embodiments.

Figure 11:
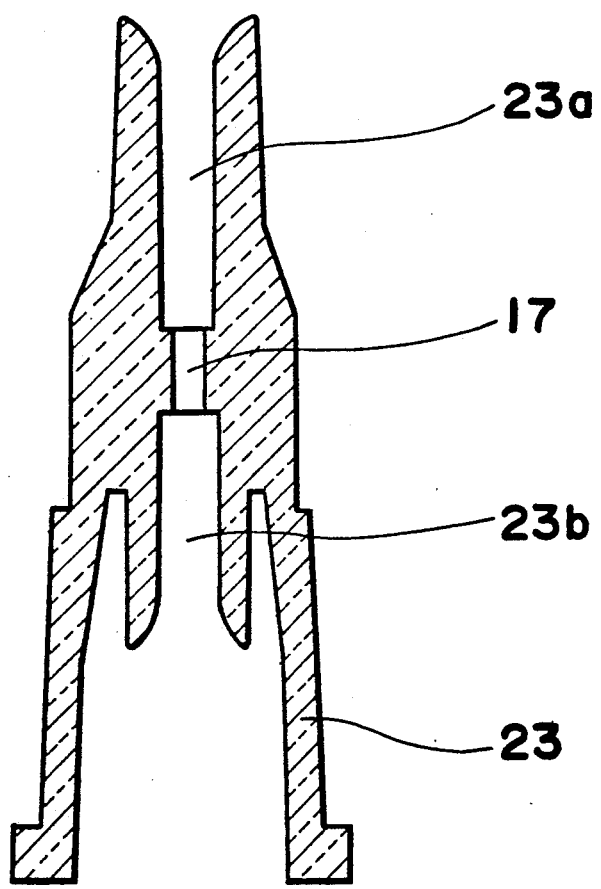
FIG. 11 is an enlarged sectional view of a luer member having a space partially defined therein and holes for adhering needles.
Figure 12:
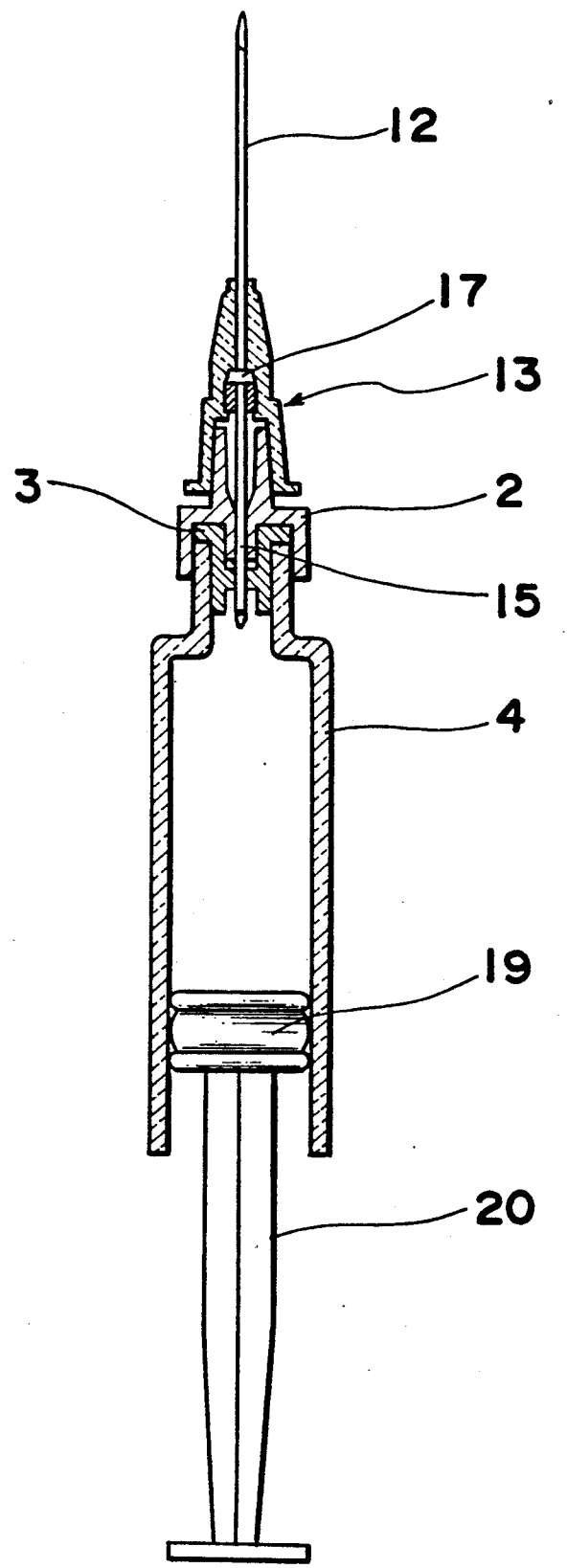
FIG. 12 is a sectional view of an injector complete for use which has a double-sided needle assembly of another embodiment fitting needles to a pre-filled syringe.

Furthermore, as shown in FIG. 11, the space 17 is previously formed in a transparent luer member 23 by one-piece molding. Thereafter, the insert needle 12 is inserted into an upper hole 23a thereof and the afflux needle 15 is inserted into a lower hole 23b thereof, with the result that a double-sided needle assembly of another embodiment can be manufactured.

Moreover, the luer members 13, 21, and 23 and the cylinder 14 can be made of plastic material such as polypropylene or polystyrene. Between the insert needle 12 and the luer 13 and between the afflux needle 15 and the luer 13, adhesives widely used in normal disposable needles can be employed. Between the plastic parts, adhesives used in normal plastic adhesion can be employed, but more preferably, both are adhered by ultrasonic welding in order to avoid to the utmost, any adverse effect to pharmaceutical liquid.

The size and length of the space 17 for observing the blood in the luer members 13, 21, and 23 is not limited as above-described, but can be modified within the scope of the present invention.

The use of the special double-sided needle assembly will be described in employing the needle assembly shown in FIG. 6. The needle assembly is inserted into the pre-filled syringe type luer cap 2 in FIG. 1 under pressure and a piston member 19 is attached to a rubber plunger 20 to be inserted into the syringe 4, resulting in completion and preparation for use.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A double-sided needle assembly comprising:
    an insert needle for insertion into a vessel;
    an afflux needle for supplying pharmaceutical liquid in a syringe of an injector to said insert needle, said afflux needle having a connecting member fixed at one end; and
    a transparent luer member having one end to which said insert needle is fixed and the other end to which the connecting member of said afflux member is fixed so that said insert needle is connected with said afflux needle through a space defined between an end of said insert needle and the connecting member of said afflux needle in said luer member, said luer member having at the other end a recess for fitting one end of the syringe to hold said insert and afflux needles on the syringe and a rib for preventing said afflux needle from slipping off from said luer member.

2. A double-sided needle assembly as claimed in claim 1, wherein said luer member is made of plastic material.

3. A double-sided needle assembly as claimed in claim 2, wherein said insert needle is fixedly inserted into a first hole of said luer member at the end, and wherein the connecting member is made of plastic and is fixed into a second hole of said luer member by an adhesive.

4. A double-sided needle assembly as claimed in claim 2, wherein said insert needle is fixedly inserted into a first hole of said luer member at the end, and wherein the connecting member is made of plastic and is fixed into a second hole of said leur member by ultrasonic welding.

* * * * *